United States Patent [19]
Kawazu et al.

[11] Patent Number: 6,136,863
[45] Date of Patent: Oct. 24, 2000

[54] ANTIFUNGAL AGENTS

[75] Inventors: Yukio Kawazu; Masayuki Yuasa; Toshimitsu Suzuki; Takuji Nakashima; Takao Itoh; Toshiro Majima, all of Yokohama, Japan

[73] Assignee: Pola Chemical Industries, Inc., Shizuloka, Japan

[21] Appl. No.: 09/131,281

[22] Filed: Aug. 7, 1998

[51] Int. Cl.$^7$ .................................................. A01N 33/02
[52] U.S. Cl. ........................... 514/647; 564/316; 564/347
[58] Field of Search .............................. 514/647; 564/316, 564/347

[56] References Cited

U.S. PATENT DOCUMENTS

| | | | |
|---|---|---|---|
| 4,247,550 | 1/1981 | Feit et al. ................................. | 424/244 |
| 5,631,401 | 5/1997 | Stein et al. ............................... | 562/451 |

FOREIGN PATENT DOCUMENTS

| | | |
|---|---|---|
| 9-208537 | 8/1997 | Japan . |
| 9-208538 | 8/1997 | Japan . |

*Primary Examiner*—Dwayne C. Jones
*Attorney, Agent, or Firm*—Oblon, Spivak, McClelland, Maier & Neustadt, P.C.

[57] ABSTRACT

This invention relates to compounds represented by the following formula (1):

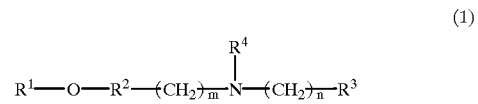

wherein $R^1$ represents a substituted or unsubstituted phenyl group, $R^2$ represents a substituted or unsubstituted phenylene group, $R^3$ represents a substituted or unsubstituted phenyl group or an aliphatic hydrocarbon group containing at least four π electrons, $R^4$ represents an alkyl group having 1 to 4 carbon atoms, and m and n individually represent integers of from 1 to 4, or salts thereof, and also to compositions containing the same. These compounds have antifungal activities and are useful as drugs.

9 Claims, No Drawings

ANTIFUNGAL AGENTS

BACKGROUND OF THE INVENTION a) Field of the Invention

This invention relates to compounds which have antifungal activities and are useful as drugs or antimicrobial materials, and also to compositions containing the same.

b) Description of the Related Art

Dermatophytosis is reckoned as one of the diseases not overcome even in these modern days, as no reliable therapy or drug has been found yet for its treatment. A large number of compounds have therefore been screened for antifungal activities. All the same, even among substances which have been found to have activities at the in vitro or animal level, all but a few remain after elimination in the actual clinical stage. At present, an extremely small number of substances are known to bring about satisfactory results. Under these circumstances, there has been a long-standing desire for the discovery of a novel base structure having antifungal activities. Incidentally, compounds represented by general formula (1), which will be described subsequently herein, are all novel compounds, to say nothing of their possession of antifungal activities.

With the foregoing circumstances in view, the present invention has as a primary object the finding of a novel base structure having antifungal activities and hence the provision of a novel compound having such antifungal activities.

SUMMARY OF THE INVENTION

Under these circumstances, the present inventors have therefore proceeded with synthesis of a wide variety of compounds and their screening for antifungal activities with a view to finding a novel base structure. As a result, such antifungal activities were found with the group of compounds represented by the formula (1), leading to the completion of the present invention.

Namely, the present invention provides a compound represented by the following formula (1):

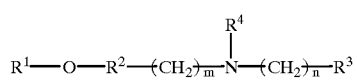

(1)

wherein $R^1$ represents a substituted or unsubstituted phenyl group, $R^2$ represents a substituted or unsubstituted phenylene group, $R^3$ represents a substituted or unsubstituted phenyl group or an aliphatic hydrocarbon group containing at least four π electrons, $R^4$ represents an alkyl group having 1 to 4 carbon atoms, and m and n individually represent integers of from 1 to 4; or a salt thereof.

The present invention also provides a composition comprising the compound of the formula (1) or the salt thereof and a carrier.

Further, the present invention also provides a method for the treatment of a mycosis, which comprises administering an effective amount of the compound of the formula (1) or the salt thereof to a patient.

Moreover, the present invention also provides use of the compound of the formula (1) or the salt thereof as a drug.

DETAILED DESCRIPTION OF THE INVENTION AND PREFERRED EMBODIMENTS

Illustrative of the substituted or unsubstituted phenyl groups represented by $R^1$ and $R^3$ in the formula (1) are unsubstituted phenyl groups and phenyl groups substituted by one or more halogen atoms, $C_1$–$C_6$ alkyl groups, $C_1$–$C_6$ alkoxyl groups, $C_1$–$C_6$ haloalkyl groups and the like. Specific examples of $R^1$ can include phenyl, chlorophenyl, fluorophenyl, methylphenyl and trifluoromethylphenyl, with phenyl being particularly preferred. Specific examples of $R^3$ can include tert-butylphenyl, phenyl, methylphenyl and chlorophenyl, with tert-butylphenyl being especially preferred.

Illustrative of the substituted or unsubstituted phenylene group represented by $R^2$ are unsubstituted phenylene groups and phenylene groups substituted by one or more halogen atoms, $C_1$–$C_6$ alkyl groups, $C_1$–$C_6$ alkoxyl groups and/or $C_1$–$C_6$ haloalkyl groups. Specific examples of $R^2$ can include 1,3-phenylene and 1,4-phenylene, with 1,3-phenylene being particularly preferred.

Illustrative of the aliphatic hydrocarbon group containing at least four π electrons, said group being represented by $R^3$, are $C_5$–$C_{12}$ aliphatic hydrocarbon groups with at least two unsaturated bonds contained therein. $C_5$–$C_{12}$ Aliphatic hydrocarbon groups containing two double bonds per group and $C_5$–$C_{12}$ aliphatic hydrocarbon groups containing one double bond and one triple bond per group are more preferred. Specific examples of these groups can include 5,5-dimethyl-1-hexen-3-yn-1-yl.

Examples of the alkyl group represented by $R_4$ can include methyl, ethyl and isopropyl, with methyl being particularly preferred.

m and n individually stand for integers of from 1 to 4, with m=1 and n=1 being especially preferred.

Among the compounds of the formula (1), N-( 4-tert-butylbenzyl)-N-methyl-3-phenoxybenzylamine and N-(6,6-dimethyl-2-hepten-4-yn-1-yl)-N-methyl-3-phenoxy-benzylamine can be mentioned as particularly preferred examples.

No particular limitation is imposed on the salt of the compound of the formula (1) insofar as it is physiologically acceptable. Preferred examples of such salts can include mineral acid salts such as the hydrochloride, sulfate and nitrate and organic acid salts such as the citrate, maleate, oxalate and tartrate. Among these salts, the hydrochloride is most preferred.

Incidentally, the compound of the formula (1) has isomers with respect to an unsaturated bond and should be considered to include the cis-isomer, the transisomer and mixtures thereof. Further, the compound of the formula (1) in the form of a hydrate, if exists, should also be considered to fall within the present invention The compound of the formula (1) can be prepared, for example, by a process represented by the following reaction scheme (A) or (B) depending on the integer represented by m.

Reaction Scheme (A)

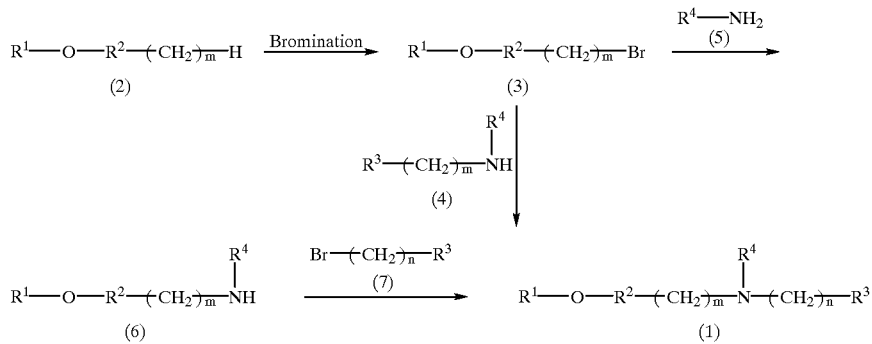

When m=1, the reaction scheme (A) is followed. A brominating agent such as N-bro-mosuccinimide is reacted with a compound (2) to obtain a compound (3). An amine (4) is then reacted with the compound (3), whereby the compound (1) of the present invention is obtained. As an alternative, the compound (2) of the present invention can also be obtained by reacting an alkylamine (5) with the compound (3) and then reacting a compound (7) with the resultant compound (6).

has been synthesized following the reaction scheme, can be easily purified in a usual manner, for example, by using a conventional purification method such as column chromatography making use of silica gel, alumina, an ion-exchange resin or the like as a carrier, liquid-liquid extraction making use of ether-water, chloroform-water, water-containing alcohol-petroleum ether or butanol-water, or recrystallization.

Reaction Scheme (B)

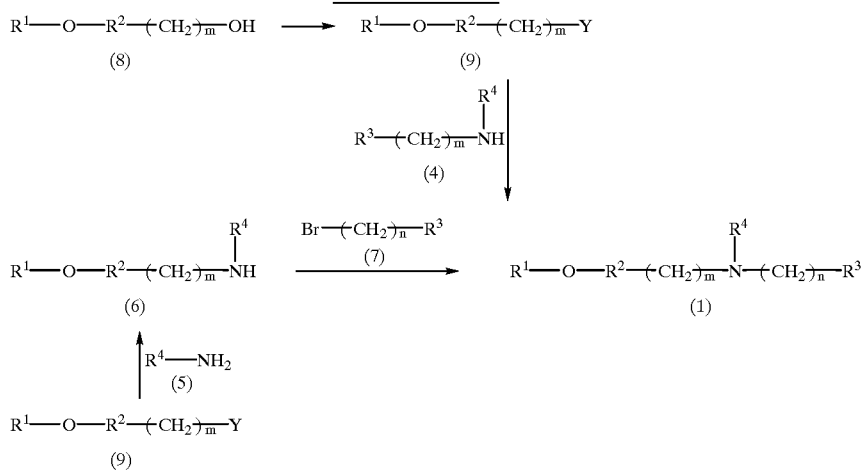

When m=2, 3 or 4, the reaction scheme (B) is followed. A compound (8) is reacted with a brominating agent such as phosphorus bromide or is tosylated to obtain a compound (9). An amine (4) is then reacted with the compound (9), whereby the compound (1) according to the present invention is obtained. As an alternative, the compound (1) of the present invention can also be obtained by reacting an alkylamine (5) with the compound (9) and then reacting a compound (7) with the resultant compound (6).

In the above-described reaction schemes (A) and (B), the reaction between each brominated or tosylated compound and its corresponding amine can be conducted preferably in the presence of a base such as sodium carbonate.

On the other hand, the physiologically-acceptable salt of the compound of the formula (1) can be prepared by a method known per se in the art, for example, by mixing the corresponding acid and the compound of the formula (1) in a nonpolar solvent or a polar solvent. The compound, which The compounds available as described above are all novel compounds which have not been reported in any publication, and have antifungal activities as will be demonstrated in Examples to be described subsequently herein. Further, the compounds of the present invention are also expected to have high stability. The compounds according to the present invention are therefore useful as antifungal agents in drugs and antifungal materials.

The composition of the present invention comprises the compound (1) and a carrier. only one of the above-described compounds may be incorporated, or two or more of them may be incorporated in combination. Illustrative of such a composition are pharmaceutical compositions such as external dermal preparations and washing and/or disinfecting external preparations, clothing such as socks, stockings and undershirts, and plastic products such as toothbrushes and ballpoint pens. Among these, pharmaceutical compositions, especially external dermal preparations, are most preferred.

To incorporate the compound of the present invention in the composition, a conventional technique can be followed. In the case of a pharmaceutical composition, for example, the compound of the present invention can be emulsified or solubilized together with other ingredients, or it can be mixed in powdery ingredients, followed by granulation. In the case of clothing, it can be mixed in a molten resin prior to spinning upon production of fibers, or the clothing can be impregnated with it. In the case of a plastic product, it is preferable to mix the compound in a molten resin. It is also possible to impregnate wood with the compound so that the wood can be protected from mold.

Examples of the carrier employed in the composition of the present invention can include any desired carriers generally contained in drugs, fibers, plastic materials and the like. Concerning pharmaceutical compositions, illustrative of such desired carriers are excipients, coloring matters, taste or smell corrigents, binders, disintegrators, coating materials, stabilizers, pH regulators, sugar-coating materials, emulsifiers, dispersants, and solubilizers. Especially for external dermal preparations, illustrative examples can include hydrocarbons such as liquid paraffin and vaseline, esters such as spermaceti and bees wax, triglycerides such as olive oil and beef tallow, higher alcohols such as cetanol and oleyl alcohol, fatty acids such as stearic acid and oleic acid, polyhydric alcohols such as propylene glycol and glycerin, nonionic surfactants, anionic surfactants, cationic surfactants, and thickeners. For clothing and plastics, illustrative examples can include plasticizers, crosslinking agents, coloring matters, antioxidants, and ultraviolet absorbers. The content of the compound of the present invention in the composition according to the present invention may range preferably from 0.001 to 20 wt. %, more preferably from 0.01 to 15 wt. %, most preferably from 0.1 to 10 wt. %.

EXAMPLES

The present invention will hereinafter be described in detail by Examples. Needless to say, the present invention shall not be limited to the Examples only.

Example 1

Preparation of N-(4-tert-butylbenzyl)-N-methyl-3-phenoxybenzylamine (Compound 1)

Following the process to be described below, Compound 1 was prepared. Namely, 10.16 g of m-phenoxytoluene, 9.82 g of N-bromosuccinimide and 0.15 g of benzoyl peroxide were weighed and added to 90 ml of carbon tetrachloride as a solvent. The resulting mixture was heated under reflux for 3 hours to conduct a reaction. The reaction mixture was allowed to cool down, the insoluble matter was filtered off, and the filtrate was then concentrated. The concentrate was purified by chromatography on a silica gel column (eluent: chloroform), whereby 10.9 g of 3-phenoxybenzyl bromide were obtained. In 20 ml of N,N-dimethylformamide, 2.79 g of N-(4-tert-butylbenzyl)methylamine and 1.67 g of sodium carbonate were mixed, to which a solution of 3.77 g of 3-phenoxybenzyl bromide in 25 ml of N,N-dimethylformamide was added dropwise under ice cooling. The temperature of the reaction mixture was allowed to rise to room temperature, at which a reaction was allowed to proceed for 12 hours. Chloroform and water were added to the reaction mixture to conduct liquid-liquid extraction. An organic layer was collected and then washed with water and a saturated aqueous solution of sodium chloride. The resulting solution was dried over anhydrous sodium sulfate and was then concentrated. The concentrate was purified by chromatography on a silica gel column (eluent:hexane:chloroform:ethyl acetate= 9:1:0→0:10:0→0:0:100). Relevant fractions were concentrated, whereby 4.49 g of N-(4-tertiary-butylbenzyl)-N-methyl-3-phenoxybenzylamine (Compound 1) were obtained (yield: 87.8%). The following is its NMR data (CDCl$_3$ δ ppm): 1.28(9H,s), 2.18(3H,s), 3.476(2H,s), 3.483 (2H,s), 6.86–7.35(13H,m).

Compound 1 was next converted into the hydrochloride. Namely, 4.49 g of Compound 1 were dissolved in 30 ml of ethyl acetate, followed by the dropwise addition of 3.5 ml of 4 N hydrochloric acid-ethyl acetate. Further, 150 ml of diethyl ether were added, and precipitated white crystals were collected. The crystals were recrystallized from a mixed solvent of diethyl ether and ethanol, whereby 4.08 g of white crystals were obtained (yield: 82.8%). The melting point of the crystals was 200–202° C. The followings are its NMR and IR data:

NMR (CDCl$_3$ δ ppm): 1.27(9H,s), 2.57(3H,d), 3.96–4.08 (2H,m), 4.17–4.28(2H,m), 7.02–7.75(13H,m), 12.8(1H,s).
IR (KBr cm$^{-1}$): 2962, 2615, 1489, 1259.

Example 2

Preparation of trans-N-(6,6-dimethyl-2-hepten-4-yn-1-yl)-N-methyl-3-phenoxybenzylamine (Compound 2) and cis-N-(6,6-dimethyl-2-hepten-4-yn-1-yl)-N-methyl-3-phenoxybenzylamine (Compound 3)

Following the process to be described below, Compound 2 and Compound 3 were prepared. Namely, 10.16 g of m-phenoxytoluene, 9.82 g of N-bromosuccinimide and 0.15 g of benzoyl peroxide were weighed and added to 90 ml of carbon tetrachloride as a solvent. The resulting mixture was heated under reflux for 3 hours to conduct a reaction. The reaction mixture was allowed to cool down, the insoluble matter was filtered off, and the filtrate was then concentrated. The concentrate was purified by chromatography on a silica gel column (eluent: chloroform), whereby 10.9 g of 3-phenoxybenzyl bromide were obtained. In 20 ml of methanol, 9.91 g of the reaction product were dissolved. The resulting solution was added dropwise under stirring to an ice-cooled 40% solution of methylamine in methanol, followed by stirring for 15 minutes under ice cooling. The temperature of the reaction mixture was allowed to rise to room temperature, at which the reaction mixture was stirred further for 42 hours. After the solvent was distilled off, 1 N dilute hydrochloric acid was added and the resulting mixture was washed with diethyl ether. A water layer was alkalinized with a 3 N aqueous solution of sodium hydroxide and was then extracted with diethyl ether. The thus-obtained diethyl ether solution was dried over magnesium sulfate and the solvent was distilled off. The residue was purified by chromatography on a silica gel column (eluent:chloroform:methanol=50:1), whereby 4.34 g of N-(3-phenoxybenzyl)methylamine were obtained. The reaction product was dissolved in 20 ml of N,N-dimethylformamide, to which 2.16 g of sodium carbonate were added. Under ice cooling, a solution of 4.0 g of 1-bromo-6,6-dimethyl-2-hepten-4-yne in 5 ml of N,N-dimethylformamide was added dropwise. The temperature of the resulting mixture was allowed to rise to room temperature, at which a reaction was allowed to proceed for 18 hours. After the reaction mixture was concentrated under reduced pressure, diethyl ether and water were added to conduct liquid-liquid extraction. An organic layer was collected and then washed with water and a saturated aqueous solution of sodium chloride. The extract was dried over anhydrous magnesium sulfate and concentrated, and the concentrate was purified by chromatography on a silica gel column (eluent:hexane:ethyl acetate=10:1). Relevant fractions were concentrated, whereby 2.92 g of trans-N-(6,6-dimethyl-2-hepten-4-yn-1-yl)-N-methyl-3-phenoxybenzylamine (Compound 2) and 1.08 g of cis-N-(6,6-dimethyl-2-hepten-4-yn-1-yl)-N-methyl-3-phenoxybenzylamine (Compound 3) were obtained, respectively (yields: 44.1% and 16.3%). The followings are their NMR data (CDCl$_3$ δ ppm):

(Compound 2)

1.24(9H,s), 2.18(3H,s), 3.03(2H,dd), 3.47(2H,s), 5.63 (1H,dt), 6.06(1H,dt), 6.88(1H,m), 6.96–7.15(5H,m), 7.22–7.40(3H,m).

(Compound 3)

1.24(9H,s), 2.22(3H,s), 3.26(2H,dd), 3.50(2H,s), 5.61 (1H,dt), 5.93(1H,dt), 6.89(1H,m), 6.95–7.15(5H,m), 7.22–7.38(3H,m).

Compound 2 was next converted into the hydrochloride. Namely, 2.92 g of Compound 2 were dissolved in 25 ml of ethyl acetate, followed by the dropwise addition of 2.4 me of 4 N hydrochloric acid-ethyl acetate. Further, 150 ml of diethyl ether were added, and precipitated white crystals were collected. The crystals were recrystallized from a mixed solvent of diethyl ether and ethanol, whereby 3.06 g of white crystals were obtained (yield: 94.4%). The melting point of the crystals was 201.5–203° C. The following is its NMR data:

NMR (δ ppm): 1.25(9H,s), 2.62(3H,d), 3.52(1H,m), 3.70 (1H,m), 3.99(1H,dd), 4.17(1H,dd), 5.80(1H,d), 6.26(1H,dt), 7.0–7.1(4H,m), 25 7.17(1H,t), 7.35–7.53(4H,m), 12.99(1H, b).

In a similar manner, 1.08 g of Compound 3 were converted into 1.06 g of the hydrochloride (yield: 88.5%). The following is its NMR data:

NMR (δ ppm): 1.25(9H,s), 2.64(3H,d), 3.70–3.93(2H,m), 4.04(1H,m), 4.23(1H,m), 5.98(1H,d), 6.27(1H,m), 6.98–7.14(4H,m), 7.17(1H,t), 7.35–7.55(4H,m), 12.96(1H, b).

Example 3

In accordance with the formulation shown below, compositions which contained polystyrene and the corresponding compounds of the present invention, respectively, were prepared. Described specifically, toothbrush handles of each composition were produced by mixing polystyrene beads and the corresponding compound of the present invention, namely, Compound 1, 2 or 3 and then subjecting the resultant mixture to melt forming.

| Polystyrene beads | 99 parts by weight |
|---|---|
| Compound 1, 2 or 3 | 1 part by weight |

Example 4

In accordance with the formulation shown below, compositions which contained polystyrene and the corresponding compounds of the present invention, respectively, were prepared. Described specifically, toothbrush handles of each composition were produced by mixing polystyrene beads and the hydrochloride of the corresponding compound of the present invention, namely, the hydrochloride of Compound 1, 2 or 3 and then subjecting the resultant mixture to melt forming.

| Polystyrene beads | 90 parts by weight |
|---|---|
| Hydrochloride of Compound 1, 2 or 3 | 10 parts by weight |

Example 5

In accordance with the formulation shown below, compositions which contained polystyrene and the corresponding compounds of the present invention, respectively, were prepared. Described specifically, ballpoint pen barrels of each composition were produced by mixing polystyrene beads and the corresponding compound of the present invention, namely, Compound 1, 2 or 3 and then subjecting the resultant mixture to melt forming.

| Polystyrene beads | 99.9 parts by weight |
|---|---|
| Compound 1, 2 or 3 | 0.1 part by weight |

Example 6

In accordance with the formulation shown below, compositions which contained polystyrene and the corresponding compounds of the present invention, respectively, were prepared. Described specifically, ballpoint pen barrels of each composition were produced by mixing polystyrene beads and the hydrochloride of the corresponding compound of the present invention, namely, the hydrochloride of Compound 1, 2 or 3 and then subjecting the resultant mixture to melt forming.

| Polystyrene beads | 99 parts by weight |
|---|---|
| Hydrochloride of Compound 1, 2 or 3 | 1 parts by weight |

Example 7

In accordance with the formulation shown below, ointments were obtained for the treatment of athlete's foot. Described specifically, an ointment of each composition was obtained by weighing the corresponding ingredients, charging them into a kneader and then kneading them there.

| Vaseline | 99 parts by weight |
|---|---|
| Compound 1, 2 or 3 | 1 part by weight |

Example 8

In accordance with the formulation shown below, ointments were obtained for the treatment of athlete's foot. Described specifically, an ointment of each composition was obtained by weighing the corresponding ingredients, charging them into a kneader and then kneading them there.

| | |
|---|---|
| Absorption ointment | 99 parts by weight |
| Compound 1, 2 or 3 | 1 part by weight |

Example 9

Liquid preparations were obtained by stirring and solubilizing the corresponding ingredients shown below.

| | |
|---|---|
| Ethanol | 92 parts by weight |
| Alkyl methacrylate copolymer | 2 parts by weight |
| Compound 1, 2 or 3 | 1 part by weight |
| Propylene glycol | 5 parts by weight |

Example 10

Antifungal Activity Test (measurement of minimum inhibitory concentration)

Antifungal activities of compounds according to the present invention against Trichophyton sp. were determined. Described specifically, *T. mentagrophytes* (TIMM1189) and *T. rubrum* (IF05808) were separately cultured at 27° C. for 2 weeks on Sabouraud dextrose agar slants in advance, whereby they were allowed to form sufficient conidia. With respect to each of the fungus strains, the conidia were washed in a sterilized physiological saline, which contained Tween 80 at a concentration of 0.05 wt./vol. %, by rubbing the conidia with a platinum loop, whereby the conidia were suspended. The suspension was filtered through a double-layer gauze so that only the conidia were collected in a form suspended in the physiological saline. The suspension was diluted to adjust the concentration of conidia to $1 \times 10^5$ conidia/ml, whereby a test fungus solution was obtained. Meanwhile, 4 mg of one of the test compounds were taken, to which 1 ml of dimethyl sulfoxide was added to prepare a stock. The stock was subjected to doubling dilution with dimethyl sulfoxide to prepare diluted drug solutions. To each well of a 96-well microplate for tissue culture, 175 µl of Sabouraud dextrose broth, 5 µl of the corresponding drug solution and 20 µl of the test fungus solution were added. Subsequent to thorough mixing, the fungus strain was cultured at 27° C. for 1 week. A minimum concentration at which its growth was completely inhibited was visually determined and was recorded as a minimum inhibitory concentration (MIC). As a result, the MICs of the hydrochlorides of Compound 1 and Compound 2 were found to be 100 µg/ml against *T. mentagrophytes* (TIMM1189) and also 100 µg/ml against *T. rubrum* (IF05808). This indicates the excellent antifungal activities of the compounds against Trichophyton sp.

What is claimed is:

1. A compound represented by the following formula (1):

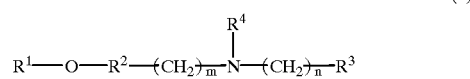

(1)

wherein $R^1$ represents a substituted or unsubstituted phenyl group, $R^2$ represents a substituted or unsubstituted phenylene group, wherein the substituent on the substituted phenylene group is one or more halogen atoms, $C_1$–$C_6$ alkyl groups, $C_1$–$C_6$ alkoxy groups and/or $C_1$–$C_6$ haloalkyl groups, $R^3$ represents a substituted or unsubstituted phenyl group or an aliphatic hydrocarbon group containing at least four π electrons, $R^4$ represents an alkyl group having 1 to 4 carbon atoms, and m and n individually represent integers of from 1 to 4; or a salt thereof.

2. A compound or a salt thereof according to claim 1, which is N-(4-tert-butylbenzyl)-N-methyl-3-phenoxybenzylamine or N-(6,6-dimethyl-2-hepten-4-yn-1-yl)-N-methyl-3-phenoxybenzylamine or a salt thereof.

3. A composition comprising a compound or a salt thereof according to claim 1 or 2 and a carrier.

4. A composition according to claim 3, which is a pharmaceutical composition.

5. A method for the treatment of a mycosis, which comprises administering an effective amount of a compound or a salt thereof according to claim 1 or 2 to a patient.

6. A compound or a salt thereof according to claim 2, which is trans-N-(6,6-dimethyl-2-hepten-4-yn-1-yl)-N-methyl-3-phenoxybenzylamine or cis-N-(6,6-dimethyl-2-hepten-4-yn-1-yl)-N-methyl-3-phenoxybenzylamine.

7. A composition comprising a compound or a salt thereof according to claim 6 and a carrier.

8. A composition according to claim 7, which is a pharmaceutical composition.

9. A method for the treatment of a mycosis, which comprises administering an effective amount of a compound or a salt thereof according to claim 6 to a patient.

* * * * *

UNITED STATES PATENT AND TRADEMARK OFFICE
CERTIFICATE OF CORRECTION

PATENT NO. : 6,136,863

DATED : October 24, 2000

INVENTOR(S): Yukio KAWAZU, et al.

It is certified that an error appears in the above-identified patent and that said Letters Patent is hereby corrected as shown below:

On the Title page, Item [73], the Assignee's residence is misspelled.
Item [73] should read as follows:

---[73] Assignee: Pola Chemical Industries, Inc., Shizuoka-shi, Japan ---

Signed and Sealed this

First Day of May, 2001

Attest:

NICHOLAS P. GODICI

*Attesting Officer*      *Acting Director of the United States Patent and Trademark Office*